United States Statutory Invention Registration [19]

[11] Reg. Number: H168

Conner [43] Published: Dec. 2, 1986

[54] HERBICIDAL SULFONAMIDES

[75] Inventor: Michael Conner, Wilmington, Del.

[73] Assignee: E. I. Du Pont de Nemours and Company, Wilmington, Del.

[21] Appl. No.: 449,547

[22] Filed: Dec. 13, 1982

[51] Int. Cl.[4] ..... A01N 43/66; A01N 43/54; C07D 251/42; C07D 239/42

[52] U.S. Cl. ..... 71/93; 71/92; 544/211; 544/212; 544/321; 544/331; 544/332

[58] Field of Search ..... 544/211; 71/93

[56] References Cited

U.S. PATENT DOCUMENTS

| | | | |
|---|---|---|---|
| 4,257,802 | 3/1981 | Levitt | 71/93 |
| 4,310,346 | 1/1982 | Levitt et al. | 544/211 |
| 4,378,991 | 4/1983 | Levitt | 544/211 |
| 4,420,325 | 12/1983 | Sauers | 544/211 |
| 4,452,628 | 6/1984 | Adams | 544/211 |
| 4,515,620 | 5/1985 | Bohner | 544/211 |
| 4,537,619 | 8/1985 | Meyer et al. | 71/93 |

FOREIGN PATENT DOCUMENTS

| | | | |
|---|---|---|---|
| 0023422 | 7/1980 | European Pat. Off. . | |
| 44808 | 1/1982 | European Pat. Off. | 544/211 |

OTHER PUBLICATIONS

A. A. Abou Ouf, et al., *J. Drug. Res.* 6, 123–129 (1974).

*Primary Examiner*—John F. Terapane
*Assistant Examiner*—Jack Thomas

[57] ABSTRACT

This invention relates to novel N-[(heterocyclic)(alkyl)-aminocarbony1]benzenesulfonamides and their use as agricultural chemicals.

17 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL SULFONAMIDES

BACKGROUND OF THE INVENTION

This invention relates to N-[(heterocyclic)(alkyl)-aminocarbonyl]benzenesulfonamides useful as agricultural chemicals.

In EPO Publication 0023422, published Feb. 4, 1981, the following compounds are taught to be herbicides, especially useful for controlling weeds in wheat.

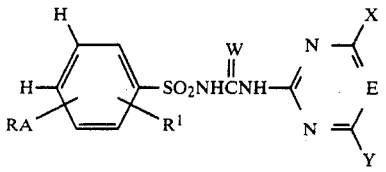

(I)

wherein

W is O or S;

R is $CHF_2$, $CF_3$, $CH_2CF_3$ or $CF_2CHFG$, where G is F, Cl, $CF_3$ or Br;

A is O or $S(O)_n$, where n is 0, 1 or 2;

$R^1$ is H, F, Cl, Br or $CH_3$;

X is $CH_3$ or $OCH_3$;

Y is $CH_3$, $OCH_3$, $OCH_2CH_3$, $(CH_2)_mOCH_3$ (where m is 1 or 2), $OCH_2CH_2OCH_3$, or $OCHR^2CO_2R^3$, where $R^2$ is H or $CH_3$ and $R^3$ is $CH_3$ or $C_2H_5$; and E is CH or N.

In U.S. Pat. No. 4,257,802, issued Mar. 24, 1981, the following compounds are taught to be herbicides and plant-growth-regulants.

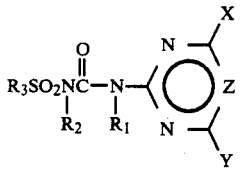

(I)

wherein $R_1$ is H, alkyl of one to three carbon atoms or $-OCH_3$;

$R_2$ is H or alkyl of one to three carbon atoms;

$R_3$ is

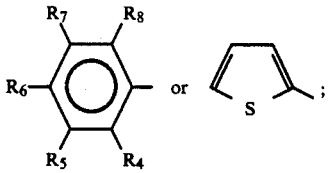

$R_4$ and $R_7$ are independently hydrogen, fluorine, chlorine, bromine, alkyl of 1–4 carbon atoms, alkoxy of 1–4 carbon atoms, nitro, $CF_3$, $CH_3S$— or $CH_3CH_2S$—;

$R_5$, $R_6$ and $R_8$ are independently hydrogen, fluorine, chlorine, bromine or methyl;

X is Cl, $CH_3$, $-CH_2CH_3$, alkoxy of one to three carbons, $CF_3$, $CH_3S$—, $CH_3OCH_2$— or $CH_3OCH_2CH_2O$—;

Y is $CH_3$ or $OCH_3$; and

Z is CH or N;

and their agriculturally suitable salts; provided that:

(a) $R_1$ and $R_2$ may not simultaneously be hydrogen;

(b) when $R_4$ and $R_8$ are both hydrogen, at least one of $R_5$, $R_6$ or $R_7$ must be hydrogen;

(c) when $R_6$ is other than H, at least one of $R_4$, $R_5$, $R_7$ and $R_8$ is other than H and at least two of $R_4$, $R_5$, $R_7$ and $R_8$ must be hydrogen; and (d) when $R_6$ is H and all of $R_4$, $R_5$, $R_7$ and $R_8$ are other than H, then all of $R_4$, $R_5$, $R_7$ and $R_8$ must be either Cl or $CH_3$.

Compounds of Formula (ii), and their use as antidiabetic agents, are reported in J. Drug. Res. 6, 123 (1974):

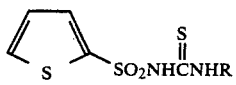

(ii)

The presence of undesired vegetation causes substantial damage to useful crops, especially agricultural products that satisfy man's basic food needs, such as soybeans, wheat and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formula I, agriculturally suitable compositions containing them and their method-of-use as preemergent or postemergent herbicides or plant growth regulants. The invention also includes the use of certain compounds of Formula I as selective herbicides, particularly on wheat and corn.

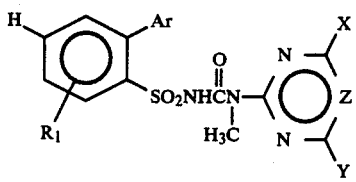

I wherein

A is O or $S(O)_n$;

R is $C_1$–$C_4$ alkyl substituted with 1–6 halogen atoms selected from 1–6 F, 0–3 Cl or 0–1 Br;

$R_1$ is H, F, Cl, Br, $CH_3$, $CF_3$ or $OCH_3$;

n is 0, 1 or 2;

X is $CH_3$ or $OCH_3$;

Y is $CH_3$, $OCH_3$, $OCH_2CH_3$, $CH_2CH_3$, $CH_2OCH_3$ or $CH_2CH_2OCH_3$; and Z is CH or N; and their agriculturally suitable salts.

Preferred for reasons of their higher herbicidal activity and/or more favorable ease of synthesis are:

(1) Compounds of Formula I where R is $CHF_2$, $CF_3$, $CH_2CF_3$, $CF_2CF_2H$, $CF_2CFHCl$, $CF_2CFHBr$, $CF_2CF_3$ or $CF_2CHFCF_3$.

(2) Compounds of Preferred 1 where $R_1$ is H.

(3) Compounds of Preferred 2 where R is $CF_3$, $CHF_2$, $CH_2CF_3$ or $CF_2CF_2H$.

(4) Compounds of Preferred 3 where A is O or S and Y is $CH_3$ or $OCH_3$.

Specifically preferred for reasons of their highest herbicidal activity and/or most favorable ease of synthesis are:

- N-[N-(4-methoxy-6-methylpyrimidin-2-yl)-N-methylaminocarbonyl]-2-(difluoromethoxy)benzenesulfonamide;
- N-[N-(4,6-dimethoxypyrimidin-2-yl)-N-methylaminocarbonyl]-2-(difluoromethoxy)benzenesulfonamide;
- N-[N-(4-methoxy-6-methyl-1,3,5-triazin-2-yl)-N-methylaminocarbonyl]-2-(difluoromethoxy)benzenesulfonamide;
- N-[N-(4,6-dimethoxy-1,3,5-triazin-2-yl)-N-methylaminocarbonyl]-2-(difluoromethoxy)benzenesulfonamide;
- N-[N-(4-methoxy-6-methylpyrimidin-2-yl)-N-methylaminocarbonyl]-2-(difluoromethylthio)benzenesulfonamide;
- N-[N-(4,6-dimethoxypyrimidin-2-yl)-N-methylaminocarbonyl]-2-(difluoromethylthio)benzenesulfonamide;
- N-[N-(4-methoxy-6-methyl-1,3,5-triazin-2-yl)-N-methylaminocarbonyl]-2-(difluoromethylthio)benzenesulfonamide;
- N-[N-(4,6-dimethoxy-1,3,5-triazin-2-yl)-N-methylaminocarbonyl]-2-(difluoromethylthio)benzenesulfonamide; and
- N-[N-(4,6-dimethoxy-1,3,5-triazin-2-yl)-N-methylaminocarbonyl]-2-(trifluoromethylthio)benzenesulfonamide.

Synthesis

As shown in Equation 1, the compounds of Formula I, wherein n is 0 or 2 can be prepared by the reaction of an appropriately substituted sulfonyl isocyanate of Formula II with an appropriately substituted 2-methylaminopyrimidine or 2-methylamino-1,3,5-triazine of Formula III, A, R, $R_1$, X, Y and Z being as previously defined.

Equation 1

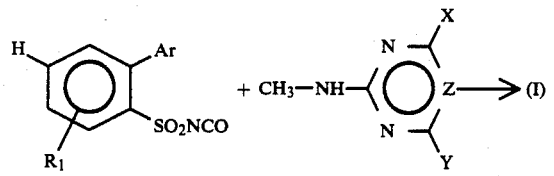

(II) (III)

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate II to a stirred suspension of amine III. Since such isocyanates are usually liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

The intermediate sulfonyl isocyanates of Formula II wherein n is 0 or 2 can be prepared as shown in Equation 2 by the reaction of the corresponding sulfonamides of Formula IV with phosgene in the presence of n-butyl isocyanate at reflux in a solvent such as xylene, according to the procedure of H. Ulrich and A. A. Y. Sayigh, *Newer Methods of Preparative Organic Chemistry*, Vol. VI, p. 223-241, Academic Press, New York and London, W. Foerst Ed. In cases where formation of the desired sulfonyl isocyanate is difficult by the above procedure, the sulfonylurea formed by the reaction of butyl isocyanate with the appropriate sulfonamide is reacted with phosgene according to the above reference.

Equation 2

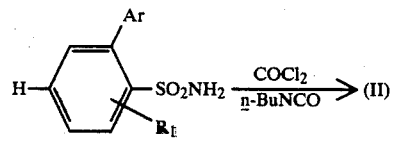

(IV)

Alternatively, the addition of a tertiary amine base such as 1,4-diaza-[2.2.2.]-bicyclooctane may catalyze the preceeding phosgenations.

Sulfonyl isocyanates can also be made by the method of Ulrich et al. [*J. Org. Chem.*, 34, 3200 (1969)]:

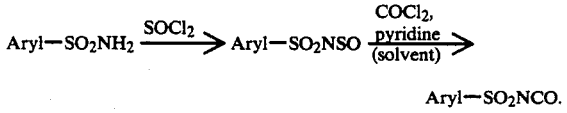

The sulfonamide is boiled under reflux with an excess of thionyl chloride until the sulfonamide protons are undetectable by proton resonance spectrum. An overnight reaction period (about 16 hours) is generally sufficient. After evaporation of the thionyl chloride, the residue is dissolved in an inert solvent, such as toluene, benzene or xylene, and a catalytic amount of pyridine. The mixture is heated to about 60°-140° (80°-100° preferred) with at least one equivalent of phosgene to yield the desired isocyanate, usually with 3 hours. The mixture containing the sulfonyl isocyanate can be used directly for the synthesis of sulfonylureas or the sulfonyl isocyanate can be purified by filtration and evaporation of the filtrate, followed by vacuum distillation.

Conversion of sulfonyl chlorides to sulfonamides, as shown in Equation 2a, is well known (e.g., L. Fieser and M. Fieser, op. cit., 699). It is convenient to dissolve the sulfonyl chloride in an inert solvent, e.g. toluene, ethyl acetate, tetrahydrofuran, etc., and pass in gaseous ammonia. Temperature is not critical and can range from about −20° to the boiling point of the solvent. For convenience, ambient temperatures are preferred.

The product can be isolated from the reaction mixture by the addition of water, evaporation of the solvent and filtration of the solid sulfonamide. If the product is soluble in the reaction mixture and the solvent is watermiscible, the product can be precipitated by addition of water and isolated by filtration.

Equation 2a

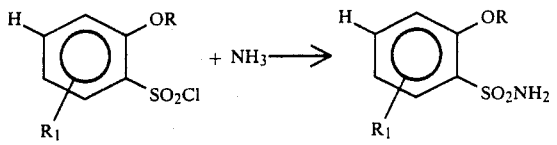

(IIa)

(Haloalkoxy)benzene derivatives can be made by methods well known in the art.

(Trifluoromethoxy)benzene derivatives can be made by the method of Sheppard [*J. Org. Chem.*, 29, 1 (1964)], e.g.:

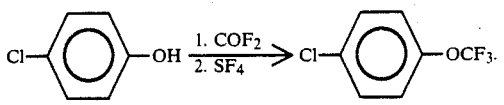

(Tetrahaloethoxy)benzene derivatives can be made by the method of England et al. [*J. Am. Chem. Soc.*, 82, 5116 (1960)], which also applies to the hexafluoropropoxy compounds, e.g.:

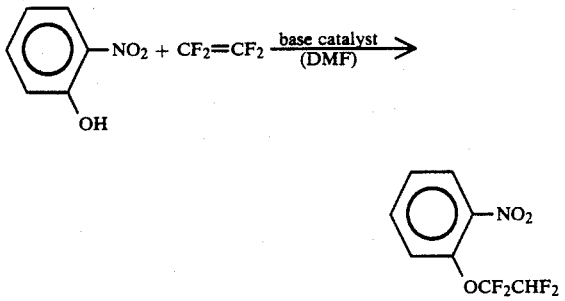

(Trifluoroethoxy)benzene derivatives can be made by reaction of trifluoroethanol with an activated aromatic halide, e.g.:

Equation 3

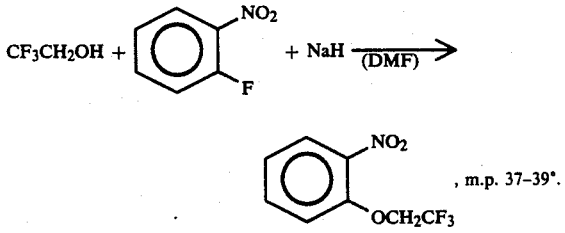

In Equation 3, sodium hydride and trifluoroethanol are mixed in an aprotic solvent, such as dimethylformamide (DMF), dioxane or tetrahydrofuran (THF), with 2-(fluoro or chloro)-1-nitrobenzene. The reaction proceeds to completion at ambient temperature. Heat may be applied (e.g., with a steam bath) if desired to speed the reaction to completion. The product is isolated by diluting the reaction mixture with water, extracting with an organic water-immiscible solvent and evaporation of the solvent. This reaction is similar to that described in Japanese Pat. No. 5 2057-320.

(Difluoromethoxy)benzene derivatives can be made by the method of Yagupolskii et al. [*Chem. Abstr.*, 70, 96318d (1969)]e.g.:

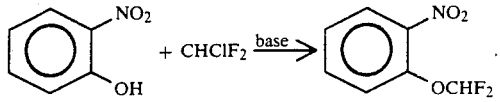

Chlorosulfonation of aromatic substrates is well known (e.g., L. F. Fieser and M. Fieser, "Advanced Organic Chemistry", 696-698, Reinhold, New York, 1961). The chlorosulfonation (Equation 4) can be accomplished by addition of the trifluoroalkoxy compound to the chlorosulfonic acid or vice versa, optionally in the presence of a cosolvent, such as an alkane or chlorinated alkane (e.g., hexane, 1-chlorobutane, methylene chloride, etc.). The reaction temperature is not critical, with a range of about −5° to 50° C. operable and ambient temperature (e.g. 20° to 30°) preferred, for convenience. At ambient temperature some hydrolysis of the trifluoromethoxy group occurs. At lower temperatures, chlorosulfonation occurs more slowly with less of the hydrolysis, while at higher temperatures, chlorosulfonation occurs more rapidly with more accompanying hydrolysis. Reaction time at ambient temperature is about 1 to 24 hours, depending on the exact substrate being chlorosulfonated, with an overnight period (about 16 hours) satisfactory. Chlorosulfonation of the tetrahaloethoxy, hexafluoropropoxy and difluoromethoxy compounds is more difficult to control without hydrolysis of the haloalkoxy group than is chlorosulfonation of the trifluoromethoxy or trifluoroethoxy compounds.

Equation 4

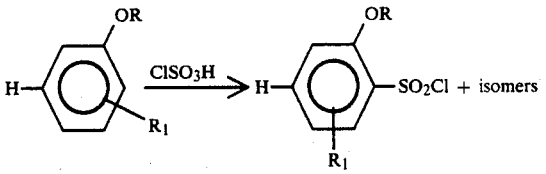

The aromatic sulfonyl chloride is conveniently isolated from the reaction mixture by pouring the mixture into ice-water, followed by extraction with a water-immiscible organic solvent in which the aromatic sulfonyl chloride is soluble. Such solvents include 1-chlorobutane, methylene chloride, 1,2-dichloroethane, ethyl acetate, toluene and diethyl ether. The solution of the sulfonyl chloride can be dried and evaporated to provide the sulfonyl chloride, which can be further purified by distillation, preferably in vacuum to suppress any thermally dependent decomposition. Alternatively, the solution of the sulfonyl chloride can be used directly in reaction with ammonia in the next step, preparation of the sulfonamide.

Chlorosulfonation can produce isomeric mixtures. Such isomeric mixtures can be separated by conventional routes (e.g., fractional distillation, chromatography) or used without separation. In the latter case, isomeric mixtures of sulfonamides, sulfonyl isocyanates and sulfonylureas are formed in the subsequent reactions. Similarly, the isomeric mixtures of intermediates formed further in the synthesis sequence can be separated or used as isomeric mixtures; isomeric mixtures of product sulfonyl(ureas and thioureas) can be used as herbicides or separated and used as individual compounds.

Sulfonyl chlorides can also be prepared, as shown in Equation 5, from aniline derivatives by diazotization, followed by reaction with sulfur dioxide and cuprous chloride. It should be emphasized that whereas chlorosulfonation is applicable to compounds where $R=CF_3$ or $CF_3CH_2$ (trifluoromethoxy or trifluoroethoxy compounds), the diazotization route (Equation 5) is of more general applicability.

Equation 5

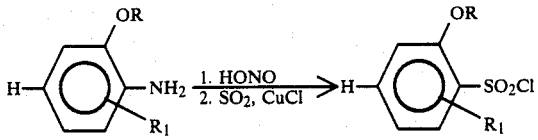

(VII) (IIa)

Aniline derivatives where R is $CF_3$, tetrahaloethyl, $HCF_2$ or hexafluoropropyl can be produced by methods described by Sheppard (op. cit.), England (op. cit.) and Yagupolskii (op. cit.). The aniline compound is diazotized according to methods well known in the art, [c.f. H. L. Yale and F. Sowinski, *J. Org. Chem.*, 25, 1824 (1960)]. The sulfonyl chloride, generally an oil, is extracted into an organic solvent, such as 1-chlorobutane, diethyl ether, toluene or ethyl acetate, the organic extract dried and evaporated to yield the sulfonyl chloride or the solution can be used directly to prepare the desired sulfonamide.

When a nitration reaction is used to make the precursor to VII, in some cases isomeric mixtures are formed, e.g.:

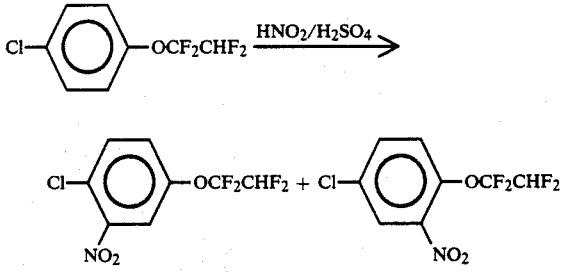

These isomeric mixtures can be separated by conventional means (e.g., fractional distillation or chromatography) or used as such; in the latter case isomeric mixtures of the aniline VII, sulfonyl chloride, sulfonamide, sulfonyl isocyanate and sulfonylures are found in the reactions which follow. Likewise, the isomeric mixtures of intermediates further in the synthesis sequence can be separated or used as the isomeric mixtures.

(Haloalkylthio, haloalkylsulfinyl and haloalkylsulfonyl)benzenesulfonylureas

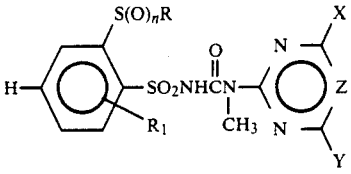

(Ib)

wherein the substituents are defined as for compound (I).

(Haloalkylthio, haloalkylsulfinyl and haloalkylsulfonyl)benzene derivatives VIIIa and VIIIb below which are used as starting materials for preparation of Ib, can be made by known methods [e.g., *Chem. Abstr.*, 70, 96324c (1969); *Chem. Abstr.*, 72, 66651f (1970); England, loc. cit.; Yagupolskii, loc. cit.].

The (trifluoroethylthio)benzenes can be made by reaction of the appropriate thiophenol with a trifluoroethylating agent, such as trifluoroethyl iodide or trifluoroethyl trichloromethanesulfonate. The thiophenol compound is reacted with powdered potassium hydroxide and trifluoroethyl iodide in an aprotic solvent such as DMF, dioxane or THF. The reaction proceeds to completion at ambient temperature. Heat (e.g., with a steam bath) may be applied to increase the reaction rate. The product is isolated as described in Equation 3 above.

Equation 6

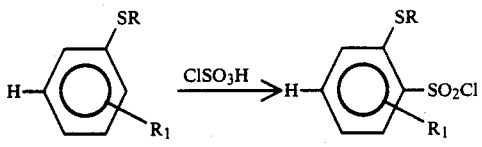

(VIIIa) (IX)

Chlorosulfonation of VIIIa proceeds in the same manner as described for the oxygen analog and is shown in Equation 6.

Equation 7

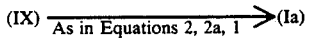

Conversion of the sulfonyl chloride sequentially to the amide, isocyanate, and sulfonylurea proceeds as described for the oxygen analogs in reactions 2, 2*a* and 1, as shown in Equation 7.

Equation 8

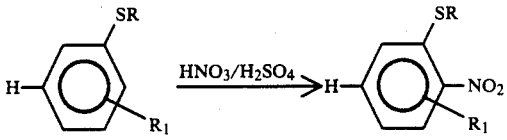

(VIIIb) (X)

The nitration is conveniently carried out by slow addition of slightly more than 1 equivalent of 90% nitric acid to a stirred, cooled (10°-30°) mixture of the sulfide VIIIb in sulfuric acid, stirring for an additional 10–45 minutes, pouring the reaction mixture into ice-water, extracting the nitro compound into a water-immiscible organic solvent (e.g., 1-chlorobutane or methylene chloride), and evaporating the solution to leave residual nitro compound, which may be further purified by vacuum distillation. Thus, the reaction is a simple mononitration of a substituted benzene ring, a reaction well known in the art.

As mentioned for the oxygen analog, nitration of VIIIb can lead to isomeric nitro compounds which, likewise, can be separated or used as such.

Equation 5

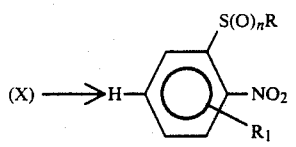

(XI)

The sulfide X is oxidized to the sulfoxide (e.g., with 20–30% $H_2O_2$ in acetic acid, 1–2 hours at 90°–100°); or the sulfide X is oxidized to the Sulfone [e.g., with chromium trioxide in acetic acid at 90°–110° during ½–2 hours]. See *Chem. Abstr.*, 70, 96324c (1969). If no oxidizing agent is used, n remains at zero and X is equal to XI.

Equation 10

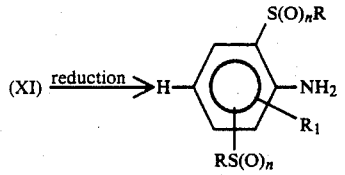

(XII)

Reduction of nitrobenzene derivatives to nitroaniline derivatives is well known in the art [e.g., W. J. Hickinbottom, "Reactions of Organic Compounds," 452–459, Longmans, London, 1959]. For example, the reduction can be accomplished by the portionwise addition of powdered iron to a mixture of the nitro compound in aqueous acetic acid at 60°–110°; followed by dilution of the reaction mixture with water and filtering off, extracting or, when n=0, steam-distilling the aniline product. Aminothiophenols can be directly tetrahaloethylated or hexafluoropropylated on the sulfur with tetrahaloethylene or hexafluoropropene to provide directly compounds XII with n=0 (England et al., loc. cit.; *Chem. Abstr.*, 75, 36584q). Also, compound XIIa is commercially available (Aldrich Chemical Co., Milwaukee, Wisc.):

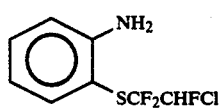

(XIIa)

Equation 11

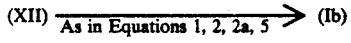

The aniline derivative XII is diazotized and converted to the sulfonyl chloride, sulfonamide, sulfonyl isocyanate and sulfonylurea as described for reactions 1, 2, 2*a* and 5.

Equation 12

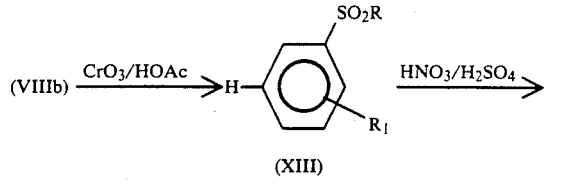

(XIII)

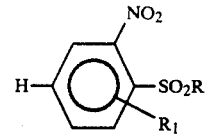

(XIIa)

As an alternate method for preparation of the intermediate nitrosulfone XIa, the sulfide VIIIb is oxidized with hydrogen peroxide as described above, XIII, followed by nitration to the nitrosulfone XIa. Nitration is accomplished with 90% nitric acid in 20% oleum at 90°–100°, the nitro group joining the ring meta to the haloalkylsulfonyl group [*Chem. Abstr.*, 53, 21766a (1959)]. The nitrosulfone XIa is converted to the sulfonylurea as already described.

Exemplary compounds within structure (I) that can be made by one or more of the described method are listed in Table I.

The synthesis of heterocyclic amine derivatives has been reviewed in "The Chemistry of Heterocyclic Compounds," a series published by interscience Pub., New York and London. 2-Methylaminopyrimidines are described by D. J. Brown in "The Pyrimidines", Vol. XVI and Vol. XVI Supplement I of the above series. 2-Amino-1,3,5-triazines can be synthesized according to the methods described by E. M. Smolin and L. Rapaport in "s-Triazines and Derivatives," Vol. XIII of the same series.

2-Methylaminopyrimidines are readily prepared by the reaction of methylamine with the appropriately substituted 2-chloropyrimidine as shown in Equation 13.

Equation 13

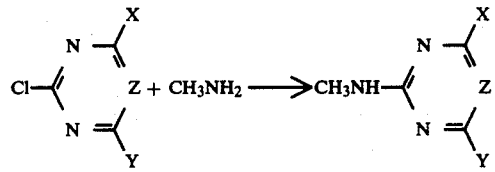

wherein

X and Y are previously defined; and

Z is CH;

(c.f. Brown, op. cit., *Supplement I*, p. 131).

Similarly, with Z=N, the reaction of Equation 13 can also be carried out, for example according to references in Smolin and Rapaport, op. cit., p. 220–221. Optionally, the method of O. Kemal and C. B. Reese, *J. Chem. Soc. Perkin I*, 1981, 1569–1573 can also be used for the preparation of N-methylaminopyrimidines and triazines used as intermediates for this invention.

In the examples which follow, all parts and percentages are by weight and all temperatures in degrees centigrade unless specified otherwise. The examples are not to be considered as limiting, but merely to exemplify the methods which can be used to prepared the compounds of this invention.

Example 1

2-Difluoromethylthio-N-[N-(4,6-dimethoxy-1,3,3-triazin-2-yl)-N-methylaminocarbonyl]benzenesulfonamide To 0.80 g of 4,6-dimethoxy-2-methylamino-1,3,5-triazine in 25 ml of dry methylene chloride was added at ambient temperature 1.33 g of 2-difluoromethylthiobenzenesulfonyl isocyanate in 15 ml of methylene chloride. The reaction mixture was stirred for 16 hours and the resultant precipitate removed by filtration. It melted at 158°-164°, showed absorption peaks by Nuclear Magnetic Resonance (60MC) at:

3.22s, N-$CH_3$;
4.08S, $(OCH_3)_2$;
6.56s, $CF_2H$; and
7.2-8.2 mult., aryl;

and showed peaks by infrared absorption spectroscopy at 1710, 1590 and 1560 $cm^{-1}$. These physical properties were all consistent for the desired structure.

Example 2

2-Difluoromethyl-N-[N-(4,6-dimethoxy-1,3,5-triazin-2-yl)-N-methylaminocarbonyl]benzenesulfonamide To 1.7 g of 4,6-dimethoxy-2-methylamino-1,3,5-triazine in 25 ml of dry methylene chloride was added with stirring at ambient temperature 2.5 g of 2-difluoromethoxybenzenesulfonyl isocyanate. The mixture was stirred, at ambient temperature, for sixteen hours and the precipitate thus formed was removed by filtration to yield the desired product melting at 164°-170°. This product showed peaks by infrared absorption spectroscopy at 1730, 1580 and 1560 $cm^{-1}$, consistent for the desired structure.

Using the procedures of Examples 1 and 2, the following compounds of Table I can readily be prepared by one skilled in the art.

TABLE I

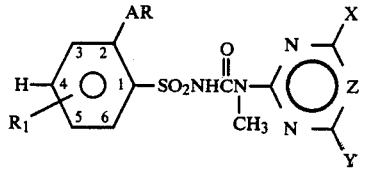

| RA | $R_1$ | Z | X | Y | m.p. (°C.) |
|---|---|---|---|---|---|
| $CF_3S$ | H | N | $OCH_3$ | $OCH_3$ | 158-160° |
| $CF_3O$ | 5-Cl | CH | $CH_3$ | $CH_3$ | |
| $HCF_2CF_2O$ | 5-Cl | CH | $CH_3$ | $CH_3$ | |
| $HCFClCF_2O$ | 5-Cl | CH | $CH_3$ | $CH_3$ | |
| $HCFBrCF_2O$ | 5-Cl | CH | $CH_3$ | $CH_3$ | |
| $CF_3CH_2O$ | 5-Cl | CH | $CH_3$ | $CH_3$ | |
| $CF_3O$ | 5-Br | CH | $CH_3$ | $CH_3$ | |
| $CF_3O$ | 5-F | CH | $CH_3$ | $CH_3$ | |
| $HCF_2CF_2O$ | 5-$CH_3$ | CH | $CH_3$ | $CH_3$ | |
| $CF_3O$ | 5-Cl | CH | $CH_3$ | $CH_3$ | |
| $CF_3O$ | 5-Cl | N | $OCH_3$ | $OCH_3$ | |
| $CF_3O$ | H | CH | $CH_3$ | $CH_3$ | |
| $CF_2HCF_2O$ | H | CH | $CH_3$ | $CH_3$ | 190-193° |
| $CF_2HCF_2O$ | H | N | $OCH_3$ | $CH_3$ | 180-183° |
| $CF_2HCF_2O$ | H | CH | $OCH_3$ | $OCH_3$ | 172-175° |
| $CF_3O$ | 5-Cl | CH | $CH_3$ | $OCH_3$ | |
| $CF_3O$ | 5-Cl | CH | $OCH_3$ | $OCH_3$ | |
| $CF_3O$ | 5-Cl | CH | $OCH_3$ | $CH_2OCH_3$ | |
| $CF_3O$ | 5-Cl | CH | $OCH_3$ | $CH_2CH_2OCH_3$ | |
| $CF_3O$ | 5-Cl | CH | $CH_3$ | $CH_2CH_2OCH_3$ | |
| $CF_3O$ | 5-Cl | CH | $CH_3$ | $OC_2H_5$ | |
| $CF_3O$ | 5-Cl | N | $CH_3$ | $CH_3$ | |
| $CF_3O$ | 5-Cl | N | $CH_3$ | $OCH_3$ | |
| $CF_3O$ | 5-Cl | N | $OCH_3$ | $OCH_3$ | |
| $CF_3O$ | 5-Cl | N | $OCH_3$ | $CH_2OCH_3$ | |
| $CF_3O$ | 5-Cl | N | $OCH_3$ | $CH_2CH_2OCH_3$ | |
| $CF_3CH_2O$ | H | CH | $CH_3$ | $CH_3$ | |
| $HCFClCF_2O$ | H | CH | $CH_3$ | $CH_3$ | |
| $HCFBrCF_2O$ | H | CH | $CH_3$ | $CH_3$ | |
| $CF_3O$ | 2-Cl | N | $OCH_3$ | $CH_2CH_2OCH_3$ | |
| $CF_3O$ | 5-Cl | N | $CH_3$ | $OC_2H_5$ | |
| $CF_3S$ | 5-Cl | CH | $CH_3$ | $CH_3$ | |
| $CF_3\overset{O}{\overset{\|}{S}}$ | 5-Cl | CH | $CH_3$ | $CH_3$ | |
| $CF_3SO_2$ | H | CH | $CH_3$ | $CH_3$ | |
| $CF_3\overset{O}{\overset{\|}{S}}$ | H | CH | $CH_3$ | $CH_3$ | |
| $CF_3SO_2$ | H | CH | $CH_3$ | $CH_3$ | |
| $CF_3S$ | H | CH | $CH_3$ | $CH_3$ | |
| $CF_2HCF_2S$ | H | CH | $CH_3$ | $CH_3$ | |

TABLE I-continued

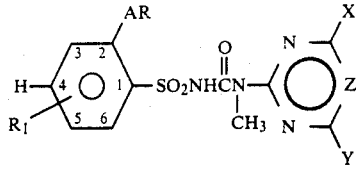

| RA | $R_1$ | Z | X | Y | m.p. (°C.) |
|---|---|---|---|---|---|
| $CFClHCF_2S$ | H | CH | $CH_3$ | $CH_3$ | |
| $CFBrHCF_2S$ | H | CH | $CH_3$ | $CH_3$ | |
| $CF_2HCF_2\overset{O}{\overset{\|}{S}}$ | H | CH | $CH_3$ | $CH_3$ | |
| $CF_2HCF_2SO_2$ | H | CH | $CH_3$ | $CH_3$ | |
| $HCF_2O$ | H | CH | $CH_3$ | $CH_3$ | |
| $CF_3CHFCF_2O$ | H | CH | $CH_3$ | $CH_3$ | |
| $CF_3CHFCF_2O$ | H | N | $OCH_3$ | $CH_3$ | |
| $CF_3CHFCF_2O$ | H | CH | $OCH_3$ | $OCH_3$ | |
| $CF_3CHFCF_2O$ | H | CH | $OCH_3$ | $CH_3$ | |
| $HCFBrCF_2O$ | 5-Br | CH | $CH_3$ | $CH_3$ | |
| $CF_2HCF_2S$ | 5-Cl | CH | $CH_3$ | $CH_3$ | |
| $CF_2HCF_2O$ | 6-$CH_3$ | CH | $CH_3$ | $CH_3$ | |
| $CHF_2S$ | H | CH | $CH_3$ | $CH_3$ | |
| $CHF_2\overset{O}{\overset{\|}{S}}$ | H | CH | $CH_3$ | $CH_3$ | |
| $CHF_2SO_2$ | H | CH | $CH_3$ | $CH_3$ | |
| $CF_3CHFCF_2S$ | H | CH | $CH_3$ | $CH_3$ | |
| $CF_3CHFCF_2\overset{O}{\overset{\|}{S}}$ | H | CH | $CH_3$ | $CH_3$ | |
| $CF_3CHFCF_2SO_2$ | H | CH | $CH_3$ | $CH_3$ | |
| $HCF_2O$ | H | CH | $OCH_3$ | $OCH_3$ | 140–148° C. |
| $HCF_2S$ | 5-$OCH_3$ | CH | $OCH_3$ | $OCH_3$ | |
| $HCF_2S$ | 6-$OCH_3$ | CH | $OCH_3$ | $OCH_3$ | |
| $HCF_2S$ | 5-$OCH_3$ | N | $CH_3$ | $OCH_3$ | |
| $HCF_2S$ | 6-$OCH_3$ | N | $CH_3$ | $OCH_3$ | |
| $HCF_2S$ | 5-$CF_3$ | CH | $OCH_3$ | $OCH_3$ | |
| $HCF_2S$ | 5-$CF_3$ | N | $CH_3$ | $OCH_3$ | |
| $HCF_2S$ | 5-F | CH | $OCH_3$ | $OCH_3$ | |
| $HCF_2S$ | 5-F | N | $CH_3$ | $OCH_3$ | |
| $HCF_2S$ | 6-F | N | $CH_3$ | $OCH_3$ | |
| $HCF_2O$ | 5-$OCH_3$ | CH | $OCH_3$ | $OCH_3$ | |
| $HCF_2O$ | 6-$OCH_3$ | CH | $OCH_3$ | $OCH_3$ | |
| $HCF_2O$ | 5-$OCH_3$ | N | $CH_3$ | $OCH_3$ | |
| $HCF_2O$ | 6-$OCH_3$ | N | $CH_3$ | $OCH_3$ | |
| $HCF_2O$ | 5-$CF_3$ | CH | $OCH_3$ | $OCH_3$ | |
| $HCF_2O$ | 5-$CF_3$ | N | $CH_3$ | $OCH_3$ | |
| $HCF_2O$ | 5-F | CH | $OCH_3$ | $OCH_3$ | |
| $HCF_2O$ | 5-F | N | $CH_3$ | $OCH_3$ | |
| $HCF_2O$ | 6-F | N | $CH_3$ | $OCH_3$ | |
| $HCF_2$ \ CFO / ClCFH | H | CH | $CH_3$ | $OCH_3$ | |
| $HCF_2$ \ CFO / ClCFH | H | N | $CH_3$ | $OCH_3$ | |
| $HCF_2$ \ CFO / ClCFH | H | CH | $OCH_3$ | $OCH_3$ | |
| $HCF_2$ \ CFO / ClCFH | H | N | $OCH_3$ | $OCH_3$ | |

TABLE I-continued

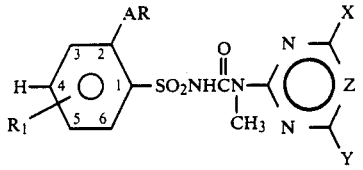

| RA | $R_1$ | Z | X | Y | m.p. (°C.) |
|---|---|---|---|---|---|
| $CF_3CH_2CH_2CH_2O$ | H | CH | $CH_3$ | $OCH_3$ | |
| $CF_3CH_2CH_2CH_2O$ | H | N | $CH_3$ | $OCH_3$ | |
| $CF_3CH_2CH_2CH_2O$ | H | CH | $OCH_3$ | $OCH_3$ | |
| $CF_3CH_2CH_2CH_2O$ | H | N | $OCH_3$ | $OCH_3$ | |
| $CH_2F-F_2C-FC(HCF_2)-O$ | H | CH | $CH_3$ | $OCH_3$ | |
| $CH_2F-F_2C-FC(HCF_2)-O$ | H | N | $CH_3$ | $OCH_3$ | |
| $CH_2F-F_2C-FC(HCF_2)-O$ | H | CH | $OCH_3$ | $OCH_3$ | |
| $CH_2F-F_2C-FC(HCF_2)-O$ | H | N | $OCH_3$ | $OCH_3$ | |
| $CF_3CFClCF_2O$ | H | CH | $CH_3$ | $OCH_3$ | |
| $CF_3CFClCF_2O$ | H | N | $CH_3$ | $OCH_3$ | |
| $CF_3CFClCF_2O$ | H | CH | $OCH_3$ | $OCH_3$ | |
| $CF_3CFClCF_2O$ | H | N | $OCH_3$ | $OCH_3$ | |
| $CF_3CF_2O$ | H | CH | $CH_3$ | $OCH_3$ | |
| $CF_3CF_2O$ | H | N | $CH_3$ | $OCH_3$ | |
| $CF_3CF_2O$ | H | CH | $OCH_3$ | $OCH_3$ | |
| $CF_3CF_2O$ | H | N | $OCH_3$ | $OCH_3$ | |
| $CF_3CF_2S$ | H | CH | $CH_3$ | $OCH_3$ | |
| $CF_3CF_2S$ | H | N | $CH_3$ | $OCH_3$ | |
| $CF_3CF_2S$ | H | CH | $OCH_3$ | $OCH_3$ | |
| $CF_3CF_2S$ | H | N | $OCH_3$ | $OCH_3$ | |
| $CF_3CHFCF_2S$ | H | CH | $CH_3$ | $OCH_3$ | |
| $CF_3CHFCF_2S$ | H | N | $CH_3$ | $OCH_3$ | |
| $CF_3CHFCF_2S$ | H | CH | $OCH_3$ | $OCH_3$ | |
| $CF_3CHFCF_2S$ | H | N | $OCH_3$ | $OCH_3$ | |
| $CF_3CHClCF_2O$ | H | CH | $CH_3$ | $OCH_3$ | |
| $CF_3CHClCF_2O$ | H | N | $CH_3$ | $OCH_3$ | |
| $CF_3CHClCF_2O$ | H | CH | $OCH_3$ | $OCH_3$ | |
| $CF_3CHClCF_2O$ | H | N | $OCH_3$ | $OCH_3$ | |
| $CH_3CH_2CH_2CHFO$ | H | CH | $CH_3$ | $OCH_3$ | |
| $CH_3CH_2CH_2CHFO$ | H | N | $CH_3$ | $OCH_3$ | |
| $CH_3CH_2CHFCHFO$ | H | CH | $CH_3$ | $OCH_3$ | |
| $CH_3CH_2CHFCHFO$ | H | N | $CH_3$ | $OCH_3$ | |
| $CF_3CH_2CH_2CHFO$ | H | CH | $CH_3$ | $OCH_3$ | |
| $CF_3CH_2CH_2CHFO$ | H | N | $CH_3$ | $OCH_3$ | |
| $FCl_2CCH_2O$ | H | CH | $CH_3$ | $OCH_3$ | |
| $FCl_2CCH_2O$ | H | N | $CH_3$ | $OCH_3$ | |
| $CF_2HO$ | H | CH | $CH_3$ | $OCH_3$ | 100–107° |
| $CF_2HO$ | H | N | $CH_3$ | $OCH_3$ | 141–148° |
| $CF_2HO$ | H | N | $OCH_3$ | $C_2H_5$ | |
| $CF_2HO$ | H | N | $CH_3$ | $OC_2H_5$ | |
| $CF_2HO$ | H | N | $OCH_3$ | $OC_2H_5$ | |
| $CF_2HO$ | H | N | $CH_3$ | $CH_2OCH_3$ | |
| $CF_2HS$ | H | CH | $CH_3$ | $CH_3$ | |
| $CF_2HS$ | H | CH | $CH_3$ | $OCH_3$ | 187–193° |
| $CF_2HS$ | H | CH | $OCH_3$ | $OCH_3$ | 173–176° |
| $CF_2HS$ | H | CH | $CH_3$ | $CH_2OCH_3$ | |
| $CF_2HS$ | H | CH | $CH_3$ | $CH_2CH_2OCH_3$ | |
| $CF_2HS$ | H | CH | $OCH_3$ | $OC_2H_5$ | |
| $CF_2HS$ | H | CH | $OCH_3$ | $C_2H_5$ | |
| $CF_2HS$ | H | N | $CH_3$ | $CH_3$ | |
| $CF_2HS$ | H | N | $CH_3$ | $OCH_3$ | 184–186° |
| $CF_2HS$ | H | N | $CH_3$ | $CH_2OCH_3$ | |
| $CF_2HS$ | H | N | $OCH_3$ | $CH_2OCH_3$ | |
| $CF_2HS$ | H | N | $CH_3$ | $OC_2H_5$ | |
| $CF_2HS$ | H | N | $OCH_3$ | $CH_2CH_2OCH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 2

| | Active Ingredient | Weight Percent* Diluent(s) | Surfactant(s) |
|---|---|---|---|
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques as demonstrated in J. E. Browning, "Agglomeration", *Chemical Engineering*, Dec. 4, 1967, pp. 147ff, and "Perry's Chemical Engineer's Handbook", 5th Ed., McGraw-Hill, New York, 1973, pp. 8-57ff.

For further information regarding the art of formulation, see for example:

H. M, Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891, 855, June 23, 1959, Col. 3, line 66 through Col. 5, line 17 and Examples 1–4;

G. C. Klingman, "Weed Control as a Science", John Wiley and Sons, Inc., New York, 1961, pp 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

Example 3

Wettable Powder

| | |
|---|---|
| N—[N—(4,6-dimethoxy-1,3,5-triazin-2-yl)-N—methylamino-carbonyl]-2-(difluoromethylthio)benzenesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

Example 4

Wettable Powder

| | |
|---|---|
| N—[N—(4,6-dimethoxy-1,3,5-triazin-2-yl)-N—methylamino-carbonyl]-2-(trifluoromethylthio)benzenesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

Example 5

Granule

| | |
|---|---|
| Wettable Powder of Example 4 | 5% |
| attapulgite granules (U.S.S. 20–40 mesh; 0.84–0.42 mm) | 95% |

A slurry of wettable powder containing ≈25% solids is sprayed on the surface of attapulgite granules in a double-cone blender. The granules are dried and packaged.

Example 6

Extruded Pellet

| | |
|---|---|
| N—[N—(4-methoxy-6-methylpyrimidin-2-yl)-N—methylaminocarbonyl]-2-(difluoromethylthio)-benzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No 20 sieve (0.84 mm openings). The granules held on a U.S.S. No. 40 sieve (0.42 mm openings) may be packaged for use and the fines recycle Exanple 7

Oil Suspension

| | |
|---|---|
| N—[N—(4,6-dimethoxy-1,3,5-triazin-2-yl)-N—methyl-aminocarbonyl]-2-(difluoromethoxy)benzenesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

Example 8

Wettable Powder

| | |
|---|---|
| N—[N—(4,6-dimethoxypyrimidin-2-yl)-N—methylamino-carbonyl]-2-(difluoromethoxy)benzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Example 9

Low Strength Granule

| | |
|---|---|
| N—[N—(4-methoxy-6-methyl-1,3,5-triazin-2-yl)-N—methyl-aminocarbonyl]-2-(difluoromethoxy)benzenesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

Example 10

Aqueous Suspension

| | |
|---|---|
| N—[N—(4,6-dimethoxy-1,3,5-triazin-2-yl)-N—methylaminocarbonyl]-2-(difluoromethylthio)-benzenesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

Example 11

Solution

| | |
|---|---|
| N—[N—(4-methoxy-6-methylpyrimidin-2-yl)-N—methylaminocarbonyl]-2-(difluoromethylthio)-benzenesulfonamide, sodium salt | 5% |
| water | 95% |

The salt is added directly to the water with stirring to produce the solution, which may then be packaged for use.

Example 12

Low Srength Granule

| | |
|---|---|
| N—[N—(4-methoxy-6-methyl-1,3,5-triazin-2-yl)-N—methylaminocarbonyl]-2-(difluoromethylthio)-benzenesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

Example 13

Granule

| | |
|---|---|
| N—[N—(4,6-dimethoxy-1,3,5-triazin-2-yl)-N—methylamino-carbonyl]-2-(trifluoromethylthio)benzenesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410-149 microns), and packaged for use.

Example 14

High Strength Concentrate

| | |
|---|---|
| N—[N—(4,6-dimethoxy-1,3,5-triazin-2-yl)-N—methyl-aminocarbonyl]-2-(difluoromethoxy)benzenesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

Example 15

Wettable Powder

| | |
|---|---|
| N—[N—(4,6-dimethoxy-1,3,5-triazin-2-yl)-N—methylamino-carbonyl]-2-(difluoromethylthio)benzenesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

Example 16

Wettable Powder

| | |
|---|---|
| N—[N—(4,6-dimethoxy-1,3,5-triazin-2-yl)-N—methylamino-carbonyl]-2-(trifluoromethylthio)benzenesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

Example 17

Oil Suspension

| | |
|---|---|
| N—[N—(4,6-dimethoxy-1,3,5-triazin-2-yl)-N—methyl-aminocarbonyl]-2-(difluoromethoxy)benzenesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

Example 18

Dust

| | |
|---|---|
| N—[N—(4,6-dimethoxypyrimidin-2-yl)-N—methylamino-carbonyl]-2-(difluoromethylthio)benzenesulfonamide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

Utility

The compounds of the present invention are active herbicides. They have utility for broadspectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, the subject compounds are useful to beneficially modify plant growth.

The rates of application for the compounds of the invention are determined by a number of factors, including their use as herbicides, or plant growth modifiers, the types of weeds to be controlled, weather and climate, formulations selected, mode of application, amount of foliage present, etc. In general terms, the subject compounds should be applied at levels of around 0.004 to 5 kg/ha, the lower rates being suggested for use on lighter soils and/or those having a low organic matter content, for plant growth modification or for situations where only short-term persistence is required.

The compounds of the invention may be used in combination with any other commercial herbicide examples of which are those of the triazine, triazole, uracil, urea, amide, diphenylether, carbamate and bipyridylium types.

The herbicidal and growth modifying properties of the subject compounds were discovered in a number of greenhouse tests. The test procedures and results follow.

Test A

Seeds of crabgrass (Digitaria sp.), barnyardgrass (*Echinochloa crusgalli*), wild oats (*Avena fatua*), sicklepod (*Cassia obtusifolia*), morningglory (Ipomoea sp.), cocklebur (Xanthium sp.), sorghum, corn, soybean, sugar beet, rice, wheat and purple nutsedge tubers (*Cyperus rotundus*) tubers were planted and treated pre-emergence with the test chemicals dissolved in a non-phytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=Chlorosis or necrosis;

E=emergence inhibition;

G=growth retardation; and

H=formative effects.

It will be seen that the compounds tested possess herbicidal and growth retarding properties.

Compounds

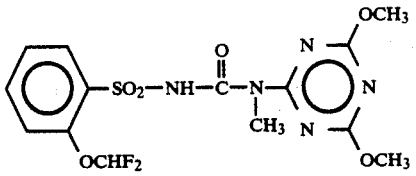

Compound 1

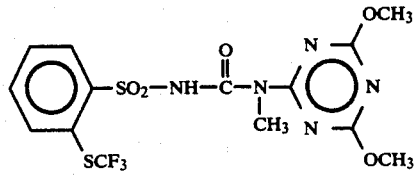

Compound 2

-continued

Compounds

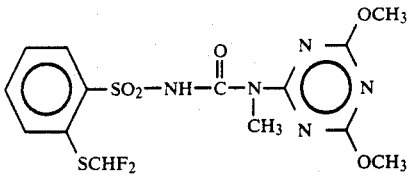

Compound 3

TABLE A

| Rate kg/ha | Cmpd. 1 0.05 | Cmpd. 2 0.05 | Cmpd. 3 0.05 |
|---|---|---|---|
| POST-EMERGENCE | | | |
| Bush bean | 2C,2H | 0 | 0 |
| Cotton | 4C,9G | 3C,7H | 2C,2H |
| Morningglory | 5C,9G | 5C,9G | 4C,8H |
| Cocklebur | 5C,9G | 4C,9G | 4C,9H |
| Sicklepod | 4C,9G | 5C,9G | 3C,8G |
| Nutsedge | 0 | 0 | 8G |
| Crabgrass | 0 | 0 | 0 |
| Barnyardgrass | 0 | 2H | 0 |
| Wild Oats | 0 | 0 | 0 |
| Wheat | 0 | 0 | 0 |
| Corn | 1H | 2C,8H | 0 |
| Soybean | 4C,9G | 3C,9G | 2C,9G |
| Rice | 0 | 4G | 0 |
| Sorghum | 0 | 2C | 0 |
| Sugar beet | 9C | 5C,9G | 9C |
| PRE-EMERGENCE | | | |
| Morningglory | 2C,5H | 9G | 4C,5G |
| Cocklebur | 5H | 8H | 9H |
| Sicklepod | 0 | 2C | 0 |
| Nutsedge | 0 | 0 | 0 |
| Crabgrass | 0 | 0 | 0 |
| Barnyardgrass | 0 | 2C | 0 |
| Wild Oats | 0 | 0 | 0 |
| Wheat | 0 | 0 | 0 |
| Corn | 0 | 2G | 0 |
| Soybean | 0 | 0 | 1H |
| Rice | 0 | 3G | 0 |
| Sorghum | 0 | 0 | 0 |
| Sugar beet | 2C,9G | 10E | 10E |

Test B

Two plastic bulb pans were filled with fertilized and limed Woodstown sandy loam soil. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with one of the test compounds within the scope of the invention.

Twenty-eight days after treatment, the plants were evaluated and visually rated for response to the chemical treatments utilizing the rating system described previously for Test A. The data are summarized in Table B.

TABLE B

PRE-EMERGENCE ON WOODSTOWN SANDY LOAM

| Rate kg/ha | Compound 3 0.06 | Compound 3 0.25 |
|---|---|---|
| Crabgrass | 4G | 4G |
| Barnyardgrass | 4G | 4G |
| Sorghum | 4G | 2G |
| Wild Oats | 3G | 2G |
| Johnsongrass | 2G | 2G |
| Dallisgrass | 0 | 0 |
| Giant foxtail | 0 | 2G |
| Ky. bluegrass | 0 | 2G |
| Cheatgrass | 0 | 2G |
| Sugar beets | 8G | 9G |
| Corn | 3G | 3G |
| Mustard | 9G | 9G |
| Cocklebur | 3G | 3G |
| Pigweed | — | — |
| Nutsedge | 2G | 4G |
| Cotton | 4G | 4G |
| Morningglory | 5G | 8G |
| Sicklepod | 0 | 2G |
| Teaweed | 2G | 2G |
| Velvetleaf | 4G | 7G |
| Jimsonweed | 2G | 4G |
| Soybean | 4G | 5G |
| Rice | 0 | 2G |
| Wheat | 0 | 2G |

Test C

The test chemical, dissolved in a non-phytotoxic solvent, was applied in an overall spray to the foliage and surrounding soil of selected plant species. One day after treatment, plants were checked for rapid burn injury. Approximately fourteen days after treatment, all species were visually compared to untreated controls and rated for response to treatment. The rating system was as described previously for Test A. The data are presented in Table C.

All plant species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and rape. All plants were sprayed approximately 14 days after planting. Additional plant species such as johnsongrass and bindweed are sometimes added to this standard test in order to evaluate unusual selectivity.

TABLE C

Over-the-Top Soil/Foliage Treatment

| Rate kg/ha | Compound 3 0.004 | Compound 3 0.015 | Compound 3 0.06 |
|---|---|---|---|
| Soybeans | 4G,3C | 7G,9C | 10C |
| Velvetleaf | 6G | 4C,7G | 9G |
| Sesbania | 8G | 9G | 9G |
| Sicklepod | 4G | 1C,8G | 3C,6G |
| Cotton | 4G | 7G | 7G |
| Morningglory | 2G | 3G,3C | 4G,3C |
| Alfalfa | 4G | 3G | 1G |
| Jimsonweed | 8G | 9G | 9G |
| Cocklebur | 2G | 3G | 6G |
| Corn | 2G | 2G | 0 |
| Crabgrass | 6G | 7G | 6G |

TABLE C-continued

| Over-the-Top Soil/Foliage Treatment | | | |
|---|---|---|---|
| | Compound 3 | | |
| Rate kg/ha | 0.004 | 0.015 | 0.06 |
| Rice | 3G | 0 | 2G |
| Nutsedge | 0 | 0 | 0 |
| Barnyardgrass | 0 | 0 | 0 |
| Wheat | 0 | 0 | 0 |
| Giant foxtail | 0 | 0 | 0 |
| Wild Oats | 0 | 0 | 0 |
| Sorghum | 0 | 0 | 0 |
| Sunflower | 6G,4C | 10C | 10C |
| Rape | 7G | 9G | 9G |
| Johnsongrass | 0 | 0 | 0 |
| Sugar beet | 9G | 10C | 10C |
| Bindweed | 0 | 0 | 0 |

Test D

Two plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and rapeseed (*Brassica napus*). The other pan was planted with seeds of Russian thistle (*Salsola kali*), cleavers (*Galium aparine*), speedwell (*Veronica persica*), kochia (*Kochia scoparia*), shepherd's purse (*Capsella bursa-pastoris*), *Matricaria inodora*, black nightshade (*Solanum nigrum*), wild buckwheat (*Polygonum convolvulus*) and sugar beets (*Beta vulgaris*). The above two pans were treated pre-emergence. At the same time two pans in which the above plant species were already growing were treated post-emergence. Plant heights at the time of treatment ranged from 1–20 cm depending on plant species.

The compound applied was diluted with a non-phytotoxic solvent and sprayed over-the-top of the pans. An untreated control and a solvent alone control were included for comparison. All treatments were maintained in the greenhouse for 19–22 days at which time the treatments were compared to the controls and the effects visually rated. The recorded data are presented in Table D.

TABLE D

| | Compound 2 | | |
|---|---|---|---|
| Rate g/ha | 1 | 4 | 15 |
| Pre-Emergence | | | |
| wheat | 0 | 0 | 0 |
| barley | 0 | 0 | 0 |
| wild oats | 0 | 0 | 0 |
| cheatgrass | 0 | 2G | 0 |
| blackgrass | 2G | 3G | 5G |
| annual bluegrass | 3G | 4G | 4G |
| green foxtail | 2G | 3G | 3G |
| Italian ryegrass | 2G | 2G | 2G |
| rapeseed | 0 | 5G | 8G |
| *Matricaria inodora* | 0 | 0 | 8G |
| *Galium aparine* | 0 | 2G | 7G |
| Russian thistle | 0 | 0 | 0 |
| shepherd's purse | 0 | 4G | 8G |
| kochia | 0 | 0 | 0 |
| black nightshade | 0 | 2G | 5G |
| speedwell | 0 | 2G | 5G |
| wild buckwheat | 0 | 1G | 4G |
| sugar beets | 0 | 5G | 9G,9C |
| Post-emergence | | | |
| wheat | 0 | 0 | 0 |
| barley | 0 | 0 | 0 |
| wild oats | 0 | 0 | 0 |
| cheatgrass | 0 | 0 | 0 |
| blackgrass | 0 | 0 | 0 |
| annual bluegrass | 0 | 0 | 0 |
| green foxtail | 0 | 0 | 0 |
| Italian ryegrass | 0 | 0 | 0 |
| rapeseed | 8G | 8G | 10C |
| *Matricaria inodora* | — | — | — |
| *Galium aparine* | — | — | — |
| Russian thistle | 0 | 0 | 0 |
| shepherd's purse | 6G | 8G | 3C,9G |
| kochia | 0 | 0 | 0 |
| black nightshade | 0 | 0 | 6G |
| speedwell | 3G | 2G | 3G |
| wild buckwheat | 0 | 3G | 8G |
| sugar beets | 4G | 6G | 5G |

What is claimed is:

1. A compound of the formula

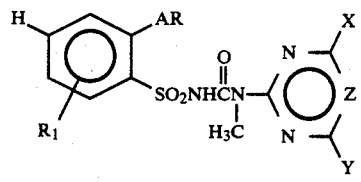

wherein

A is O or $S(O)_n$;

R is $CHF_2$, $CF_3$, $CH_2CF_3$, $CF_2CF_2H$, $CF_2CFHCl$, $CF_2CFHBr$, or $CF_2CHFCF_3$;

$R_1$ is H, F, Cl, Br, $CH_3$, $CF_3$ or $OCH_3$;

n is 0, 1 or 2;

X is $CH_3$ or $OCH_3$;

Y is $CH_3$, $OCH_3$, $OCH_2CH_3$, $CH_2CH_3$, $CH_2OCH_3$ or $CH_2CH_2OCH_3$; and Z is CH or N; and their agriculturally suitable salts.

2. Compounds of claim 1 where $R_1$ is H.

3. Compounds of claim 2 where R is $CF_3$, $CHF_2$, $CH_2CH_3$ or $CF_2CF_2H$.

4. Compounds of claim 3 where A is O or S and Y is $CH_3$ or $OCH_3$.

5. The compound of claim 1 which is N-[N-(4-methoxy-6-methyl-1,3,5-triazin-2-yl)-N-methylaminocarbonyl]-2-(difluoromethoxy)benzenesulfonamide.

6. The compound of claim 1 which is N-[N-(4,6-dimethoxy-1,3,5-triazin-2-yl)-N-methylaminocarbonyl]-2-(difluoromethoxy)benzenesulfonamide.

7. The compound of claim 1 which is N-[N-(4-methoxy-6-methyl-1,3,5-triazin-2-yl)-N-methylaminocarbonyl]-2-(difluoromethylthio)benzenesulfonamide.

8. The compound of claim 1 which is N-[N-(4,6-dimethoxy-1,3,5-triazin-2-yl)-N-methylaminocarbonyl]-2-(difluoromethylthio)benzenesulfonamide.

9. The compound of claim 1 which is N-[N-(4,6-dimethoxy-1,3,5-triazin-2-yl)-N-methylaminocarbonyl]-2-(trifluoromethylthio)benzenesulfonamide.

10. A composition suitable for controlling the growth of undesired vegetation which comprises an effective amount of a compound of claim 1 and at least one of the following: surfactant, solid or liquid diluent.

11. A composition suitable for controlling the growth of undesired vegetation which comprises an effective amount of a compound of claim 2 and at least one of the following: surfactant, solid or liquid diluent.

12. A composition suitable for controlling the growth of undesired vegetation which comprises an effective amount of a compound of claim 3 and at least one of the following: surfactant, solid or liquid diluent.

13. A composition suitable for controlling the growth of undesired vegetation which comprises an effective amount of a compound of claim 4 and at least one of the following: surfactant, solid or liquid diluent.

14. A method for controlling the growth of undesired vegetation which comprises applying to the locus to be protected an effective amount of a compound of claim 1.

15. A method for controlling the growth of undesired vegetation which comprises applying to the locus to be protected an effective amount of a compound of claim 2.

16. A method for controlling the growth of undesired vegetation which comprises applying to the locus to be protected an effective amount of a compound of claim 3.

17. A method for controlling the growth of undesired vegetation which comprises applying to the locus to be protected an effective amount of a compound of claim 4.

* * * * *